(12) United States Patent
Endoh et al.

(10) Patent No.: US 6,593,231 B2
(45) Date of Patent: Jul. 15, 2003

(54) PROCESS OF MANUFACTURING ELECTRON MICROSCOPIC SAMPLE AND PROCESS OF ANALYZING SEMICONDUCTOR DEVICE

(75) Inventors: Tetsuo Endoh, Natori (JP); Fujio Masuoka, 2-33-18, Higashikatsuyama, Aoba-ku, Sendai-shi, Miyagi (JP), 981-0923; Takuji Tanigami, Fukuyama (JP); Takashi Yokoyama, Sendai (JP); Noboru Takeuchi, Sendai (JP)

(73) Assignees: Fujio Masuoka, Miyagi (JP); Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 10/093,712

(22) Filed: Mar. 11, 2002

(65) Prior Publication Data

US 2002/0137350 A1 Sep. 26, 2002

(30) Foreign Application Priority Data

Mar. 14, 2001 (JP) .................. 2001-072339

(51) Int. Cl.[7] .................................. H01L 21/4763
(52) U.S. Cl. .................................. 438/637
(58) Field of Search .................. 438/14, 597, 637, 438/243, 314

(56) References Cited

U.S. PATENT DOCUMENTS

| 5,028,780 A | 7/1991 | Kaito et al. |
| 5,491,113 A | 2/1996 | Murota |
| 5,916,453 A | 6/1999 | Beilin et al. |
| 6,025,244 A | 2/2000 | Lee et al. |
| 6,143,646 A | * 11/2000 | Wetzel ................ 438/637 |
| 6,159,786 A | 12/2000 | Chiang et al. |
| 6,458,680 B2 | * 10/2002 | Chung ................ 438/597 |

FOREIGN PATENT DOCUMENTS

| EP | 0 284 840 A2 | 10/1988 |
| JP | 5-180739 A | 7/1993 |
| JP | 10-70098 A | 3/1998 |
| JP | 11-251385 A | 9/1999 |

OTHER PUBLICATIONS

Anonymous, "Method of Preparing TEM Plan View Sections on Semiconductor Devices", Research Disclosure, No. 437, Sep. 1, 2000, 1700, XP002203820, article No. 437125.
EP Search Report mailed Jul. 18, 2002.

* cited by examiner

Primary Examiner—Johm F. Niebling
Assistant Examiner—Andre C Stevenson
(74) Attorney, Agent, or Firm—Nixon & Vanderhy P.C.

(57) ABSTRACT

A process of manufacturing an electron microscopic sample comprising the steps of: (a) forming a mask layer for covering an object region to be analyzed of a semiconductor layer and/or a conductive layer which have/has been patterned into a desired configuration; (b) reducing a periphery region surrounded the object region to be analyzed in a depth direction by using the mask layer; (c) removing the mask layer and forming an etch stop layer over the object region to be analyzed and the periphery region; and (d) polishing the semiconductor layer and/or the conductive layer in the object region to be analyzed down to the level of the surface of etch stop layer lying on the reduced periphery region.

8 Claims, 8 Drawing Sheets

PROCESS OF MANUFACTURING ELECTRON MICROSCOPIC SAMPLE AND PROCESS OF ANALYZING SEMICONDUCTOR DEVICE

CROSS-REFERENCE TO RELATED APPLICATION

This application is related to Japanese application No. 2001-072339 filed on Mar. 14, 2001, whose priority is claimed under 35 USC §119, the disclosure of which is incorporated by reference in its entirety.

BACKGROUND OF THE INVENTION

1. Field of the Invention

The present invention relates to a process of manufacturing an electron microscopic sample and a process of analyzing a semiconductor device. In particular, it relates to a process of manufacturing an electron microscopic sample suitable for observation of a certain region on a semiconductor substrate on which a semiconductor device is in the course of its manufacture, and a process of analyzing the semiconductor device.

2. Description of Related Art

A configuration (profile) of a semiconductor device has conventionally been analyzed by the following method, for example. First, a silicon wafer on which the semiconductor device has been formed or is being formed is cleaved slightly and then a silicon wafer segment is cut out of the silicon wafer. The segment is subjected to polishing, etching by using FIB (focused ion beam) and the like to form a sample for the analysis and a plane and a section of the sample are analyzed by using a SEM (scanning electron microscope).

According to the method, however, an alignment accuracy for manufacturing the analysis sample is about ±0.5 mm. Therefore, it has been different to form a sample for analyzing a certain region with an accuracy less than 1 μm.

In this aspect, Japanese Unexamined Patent Publication No. Hei 5(1993)-187039 proposes a process of manufacturing an electron microscopic sample with the alignment accuracy improved to about ±0.1 μm.

According to the process, a high-speed rotary blade is aligned with a certain region of a silicon wafer on which semiconductor devices have been formed or are being formed, while observing through a high performance microscope. Then, a wafer segment including the certain region is cut out and processed by using the high speed rotary blade such that only a small surface portion remains. Thereafter, the remaining small surface portion is further thinned by using a focused-charged-particle-beam apparatus to prepare an analysis sample. In this step, to shorten a period for processing with the apparatus and to prevent damage to the analysis sample during the processing, the processing width and depth of the wafer segment are limited as small as possible.

However, since this method involves manual operations such as an absolute alignment and the etching while observing through the high performance microscope, there still remain problems such as the processing for preparing the analysis sample takes a long time.

In general, a photoresist technique has been utilized for patterning during the manufacture of a semiconductor device. According to the general photoresist technique, edges of the resulting pattern are rounded as compared with those of the intended design. As the semiconductor device is minimized, the edges of the resulting pattern are further rounded. In particular, in the case of STI (Shallow Trench Isolation) in which grooves are formed in a semiconductor substrate by the photoresist technique and an oxide film is formed in the grooves by thermal oxidation, edges of the groove are rounded and the growth speed of the oxide film depends on the plane orientation of the groove, so that the device characteristics are greatly influenced.

SUMMARY OF THE INVENTION

In view of the above-mentioned problems, the present invention has been achieved to provide a process of easily manufacturing an electron microscopic sample for analyzing a plane configuration of a semiconductor device by using an electron microscope with very high accuracy with respect to a certain region, without cleaving the wafer, and a process of analyzing the plane configuration and synthesizing data obtained by the analysis to obtain a three-dimensional configuration.

According to the present invention, provided is a process of manufacturing an electron microscopic sample comprising the steps of:

(a) forming a mask layer for covering an object region to be analyzed of a semiconductor layer and/or a conductive layer which have/has been patterned into a desired configuration;

(b) reducing a periphery region surrounded the object region to be analyzed in a depth direction by using the mask layer;

(c) removing the mask layer and forming an etch stop layer over the object region to be analyzed and the periphery region; and (d) polishing the semiconductor layer and/or the conductive layer in the object region to be analyzed down to the level of the surface of etch stop layer lying on the reduced periphery region.

Further, according to the present invention, provided is a process of analyzing a semiconductor device wherein a plurality of plane configurations of the semiconductor device are observed by using an electron microscopic sample obtained by the above-described process and the obtained data is synthesized to analyze a three-dimensional configuration of the semiconductor device.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

According to the process of manufacturing the electron microscopic sample of the present invention, first, in the step (a), a mask layer is formed to cover an object region to be analyzed of a semiconductor layer and/or a conductive layer that have/has been patterned in a desired configuration.

The semiconductor layer herein signifies any semiconductor substrate generally used in a semiconductor device, e.g., substrates made of element semiconductors such as silicon, germanium and the like, substrates made of compound semiconductors such as GaAs, InGaAs, ZnSe and the like. The semiconductor layer may also be semiconductor films formed on a substrate, e.g., monocrystalline semiconductor films, polycrystalline semiconductor films and amorphous semiconductor films.

The conductive film may be a single layer film or a multilayer film of: metals such as gold, platinum, silver, copper and aluminum or alloys thereof; refractory metals such as titanium, tantalum and tungsten; and silicides and polycides with refractory metals.

The semiconductor layer or the conductive layer can be formed by various methods such as CVD, sputtering, vapor deposition and the like. The semiconductor layer or the conductive layer that has been patterned signifies a semiconductor substrate on which grooves are formed, a semiconductor film or a conductive film which is formed on a substrate and patterned into electrodes or wirings. The patterning is carried out by a known method such as photolithography and etching. Specifically, in order to form the semiconductor substrate provided with the grooves, a polysilicon film, an amorphous silicon film, a silicon oxide film, a silicon nitride film or a layered film thereof is formed on the entire surface of the semiconductor substrate and openings corresponding to the grooves are formed in the film by using a resist pattern of a desired configuration. After the resist pattern is removed, the semiconductor substrate is dug using the film as a mask.

In order to pattern the conductive layer into the electrodes, a resist pattern of a desired configuration is formed on the conductive layer that has been formed on the entire surface of the substrate, and then the conductive layer is etched while using the resist pattern as a mask.

The size, shape, position and the like of the object region are suitably determined depending on what is analyzed and the type and performance of the semiconductor device to be obtained. One or more object regions may be formed in a single semiconductor device or on a single wafer.

The mask layer for covering the object region may be made of any material as long as the material is capable of protecting the object region. Examples of the mask layer include a resist film, a silicon film, a silicon oxide film, a silicon nitride film and the like which are single-layered or multilayered. The mask layer may be formed by a method known in the art, e.g., photolithography and etching, EB writing and the like.

In the step (b), a periphery region around the object region is reduced in a depth direction. A method therefor is suitably selected depending on the material of the surface of the periphery region. Examples thereof include wet etching using hydrofluoric acid, hot phosphoric acid, nitric acid, sulfuric acid or the like, dry etching such as RIE, and CMP (chemical mechanical polishing). Among them, RIE is preferable.

The periphery region herein signifies a region surrounding the object region. The size, shape and position thereof are suitably selected depending on the size and the like of the object region.

A reduction amount of the periphery region is suitably adjusted depending on the patterning depth (height) of the semiconductor layer or the conductive layer that has been patterned in the desired configuration. The reduction amount is preferably smaller than the patterning depth and controlled by a method commonly employed in the art. For example, in the case of reduction by RIE, the reduction amount is controlled by time.

If a plurality of object regions are defined as described above, a plurality of periphery regions are also produced. In such a case, the plural periphery regions may be reduced by the same amount, but preferably by different amounts. Although the reduction amount is not particularly limited, it is suitable to vary the reduction amount within the range of about 10 to 100 nm in order to accurately analyze the three-dimensional configuration of the semiconductor layer or the conductive layer that has been patterned in the desired configuration.

In the step (c), the mask layer is removed and an etch stop layer is formed over the object region and the periphery region. The mask layer may be removed by a method known in the art, e.g., exfoliation using acid or alkali, ashing and the like.

The etch stop layer is capable of protecting the semiconductor layer and the conductive layer in the periphery region surrounding the object region or the substrate surface on which the layers are formed. It is at least preferable that the etch stop layer is formed of a material having an etching rate smaller than that of the semiconductor layer and the conductive layer patterned into the desired configuration. Further, if a buried film which will be mentioned later is formed on the etch stop layer, it is preferable that the flattening of the buried film is stopped by the etch stop layer. The etch stop layer may suitably be selected depending on the kind of the semiconductor layer or the conductive layer that has been patterned in the desired configuration and the kind of the buried film. For example, a silicon nitride film may be used as the etch stop layer. A thickness of the etch stop layer is suitably about 100 to 1000 nm.

On the etch stop layer, a film to be buried in the patterned semiconductor layer or conductive layer may be formed. Further, the film may be etched to be flush with the partially surface of the etch stop layer so that it is buried completely in the semiconductor layer or the conductive layer that has been patterned. The film may be a silicon oxide film. A thickness of the film is suitably adjusted depending on the patterning depth of the semiconductor layer or the conductive layer that has been patterned in a desired configuration. The film is formed to have a thickness preferably greater than a thickness obtained by subtracting the thickness of the etch stop layer from the patterning depth, or greater than the patterning depth of the semiconductor layer or the conductive layer that has been patterned in a desired configuration. Specifically, the thickness is about 100 to 1000 nm.

The film is buried preferably by flattening such that the etch stop layer is partially exposed. The flattening is carried out by any method such as wet etching, dry etching and CMP as mentioned above. Among them, CMP is preferable.

Where the film is formed on the etch stop layer and buried by flattening such that the etch stop layer is partially exposed, the partially exposed etch stop layer is preferably removed. The removal is carried out by any method such as wet etching, dry etching, CMP and the like as mentioned above.

In the step (d), the semiconductor layer and/or the conductive layer lying on the object region are/is polished. The semiconductor layer and/or the conductive layer are/is polished to the level of the etch stop layer lying on the periphery region so that it is flush with the periphery region that has been reduced in the previous step. The polishing is carried out in the same manner as the above-mentioned flattening.

According to the process of analyzing the semiconductor device of the present invention, a plane configuration of the polished semiconductor layer and/or conductive layer in the object region are/is analyzed by using the thus obtained electron microscopic sample.

The analysis is carried out by using any apparatus as long as it is capable of observing the plane configuration. For example, a critical dimension measurement SEM, a TEM and the like may be used.

If a plurality of object regions are formed and polished by different amounts, respectively, i.e., they are polished down to different points in a depth direction, the plural configurations are observed and the obtained data is synthesized or accumulated, thereby a three-dimensional configuration is easily analyzed.

Incidentally, where a plurality of object regions are formed, it is preferably that object regions have a repeated pattern of the semiconductor layer and/or conductive layer.

Hereinafter, the process of manufacturing the electron microscopic sample of the present invention is described in detail by way of examples.

EXAMPLE 1

Figure 1:
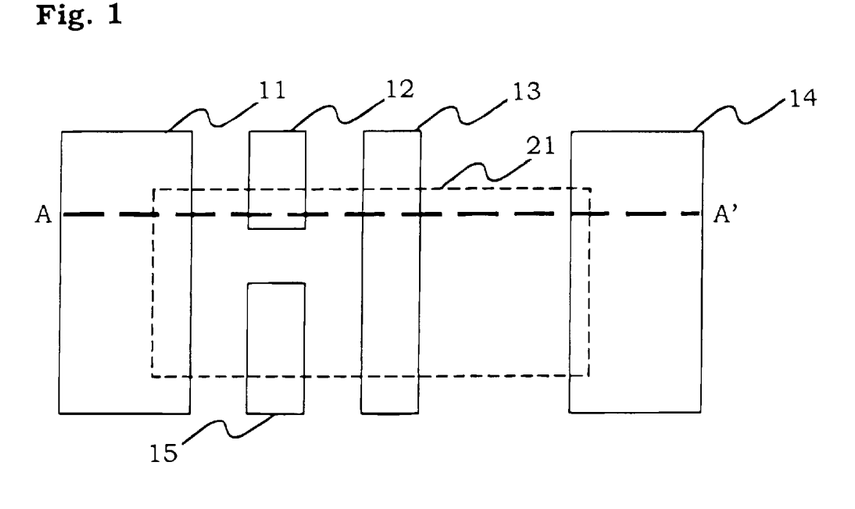
FIG. 1 is a plan view of a light exposure mask pattern for defining active regions used in a process of manufacturing an electron microscopic sample according to the present invention.

Explanation is given to a process of preparing an electron microscopic sample from a semiconductor device in which trench device isolation regions are formed by using a light exposure mask pattern for defining device isolation regions as shown in FIG. 1.

First, on a surface of a p-type silicon substrate 100 provided as a semiconductor substrate, a silicon nitride film 200 of about 200 to 1000 nm thick is deposited as a first mask layer and a polysilicon film 300 of about 50 to 500 nm thick is deposited as a second mask layer. A resist is then applied thereon.

Figure 2:
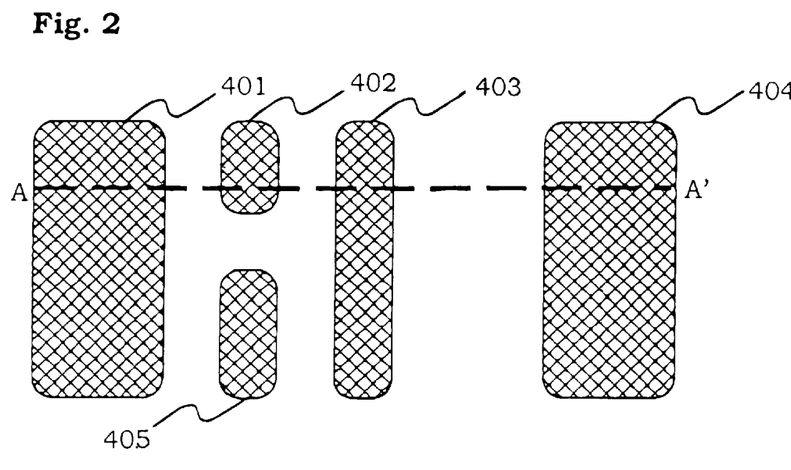
FIG. 2 is a plan view of a resist pattern formed by using the light exposure mask pattern shown in FIG. 1.
Figure 3:
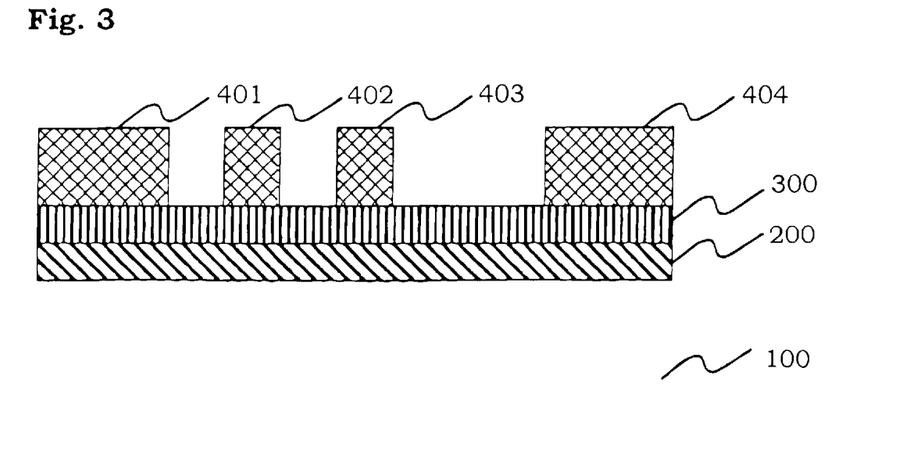
FIGS. 3 to 11 are schematic sections of a major part for illustrating the process of manufacturing the electron microscopic sample of Example 1 according to the present invention.

Then, by using a light exposure mask pattern for defining active regions 11 to 15 each having a desired configuration as shown in FIG. 1, the resist is patterned by known photolithography and etching to leave resist films 401 to 405 as shown in FIGS. 2 and 3. A region including the active regions 11 to 15 is defined as an analysis region 21 (FIG. 1).

Figure 4:
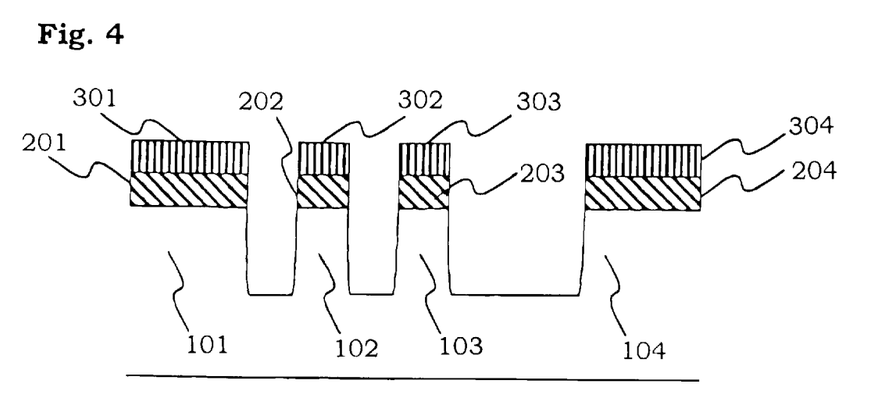

Then, using the obtained resist films 401 to 405 as a mask, the polysilicon film 300 is subjected to RIE to form mask layers 301 to 305 (305 is not shown) as shown in FIG. 4. The resist films 401 to 405 are removed, and then the silicon nitride film 200 is etched by using the mask layers 301 to 305 as a mask to form mask layers 201 to 205 (205 is not shown). Further, the silicon substrate 100 is subjected to RIE to form grooves having a depth of about 200 to 4000 nm by using the mask layers 301 to 305 and 201 and 205 as a mask. The grooves will serve as device isolation regions. Thus, silicon substrate regions 101 to 104 including the active regions are provided.

Figure 5:
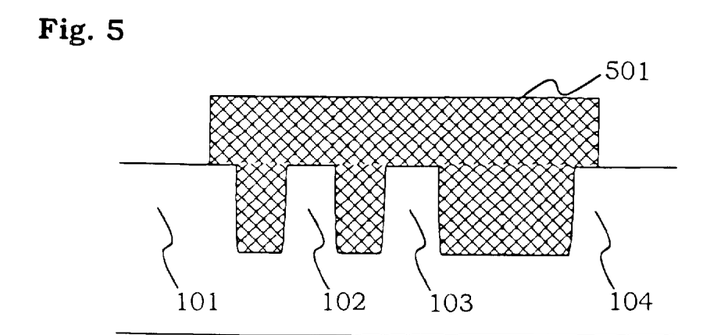

Then, the mask layers 301 to 305 and 201 to 205 are removed and a resist film 501 is formed to protect the analysis region as shown in FIG. 5.

Figure 6:
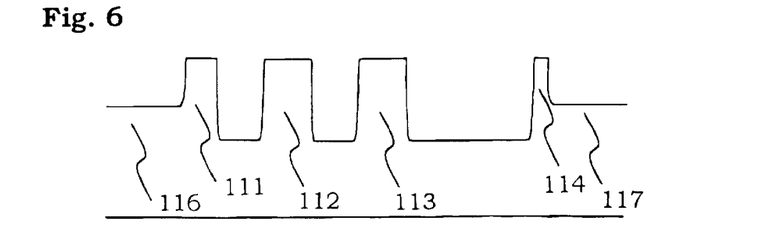

Using the resist film 501 as a mask, RIE, for example, is performed to reduce the silicon substrate 100 on the periphery of the analysis region by a thickness of about 100 nm while controlling the etching time, thereby forming silicon substrate regions 116 and 117 as shown in FIG. 6. In this step, the silicon substrate regions 116 and 117 are accurately provided while defining the etching depth with an alignment error of about 3 nm. Further, silicon substrate regions 111 to 115 in the analysis region (115 is not shown) are protected by the resist film 501 against RIE.

Figure 7:
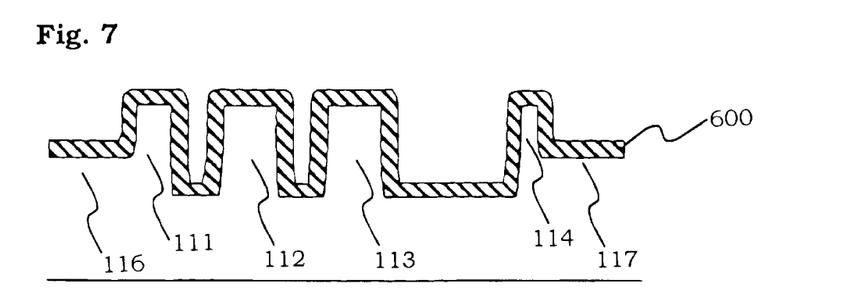

Then, as shown in FIG. 7, a silicon nitride film 600 of about 10 to 200 nm thick, which serves as a third mask layer and a polish stop layer, is deposited on the substrate including the silicon substrate regions 111 to 117.

Figure 8:
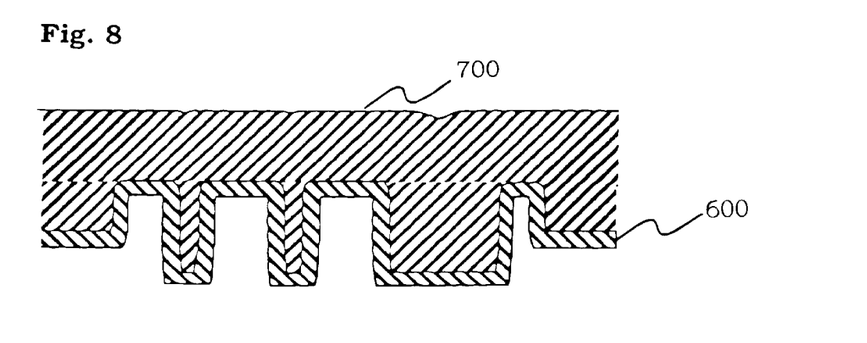

Further, as shown in FIG. 8, a silicon oxide film 700 of about 100 to 1000 nm is deposited as a fourth mask layer on the silicon nitride film 600 such that it fills the grooves in the semiconductor substrate.

Figure 9:
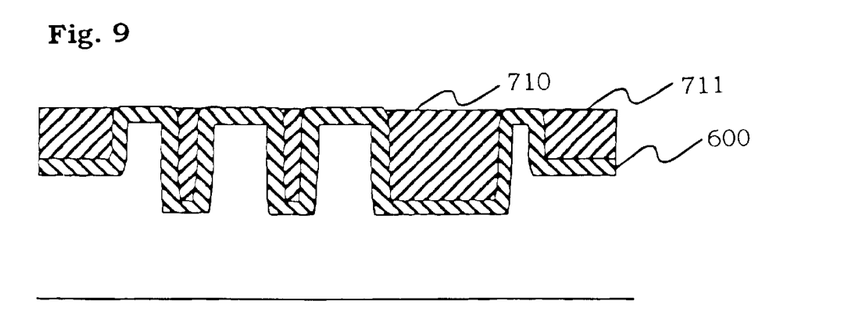

Then, the silicon oxide film 700 is etched back such that the silicon nitride film 600 is partially exposed, thereby silicon oxide films 710 are buried in the grooves in the semiconductor substrate and silicon oxide films 711 are buried in the periphery regions of the analysis region as shown in FIG. 9.

Figure 10:
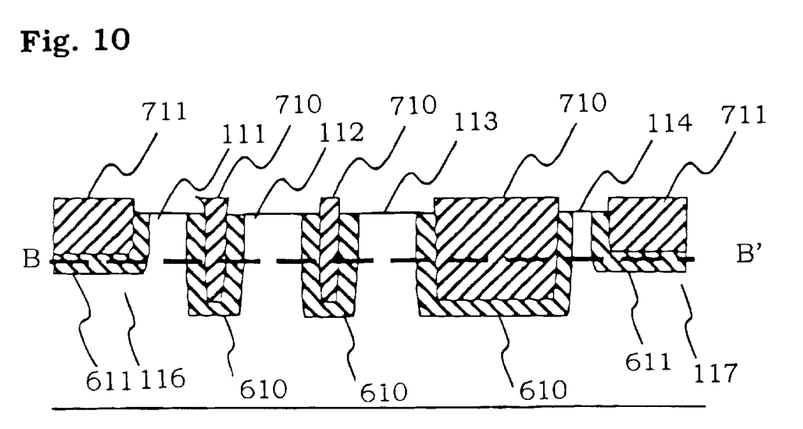

Then, using the silicon oxide films 710 and 711 as a mask, the exposed silicon nitride film 600 is selectively removed until the surfaces of the silicon substrate regions 111 to 117 are exposed to form silicon nitride films 610 and 611 as shown in FIG. 10.

Figure 11:
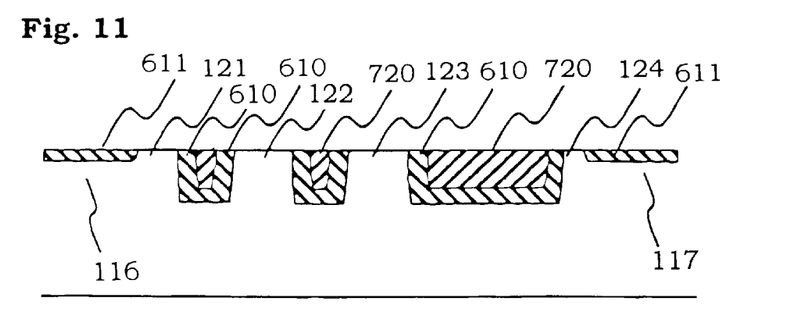

Then, as shown in FIG. 11, the silicon substrate regions 111 to 114, the silicon oxide films 710 and 711 as well as the silicon nitride films 610 and 611 are subjected to CMP, for example, such that they are polished down to the level indicated by the broken line B–B' shown in FIG. 10. In this step, the silicon nitride films 610 and 611, which serve as the third mask layers and the polish stop layers and located on the sides of the grooves in the semiconductor substrate in the analysis region, are polished by CMP at almost the same polish rate as the adjacent silicon substrate regions 111 to 114 and the silicon oxide films 710 and 711. When the silicon nitride films 611 formed on the semiconductor surface regions 116 and 117 are exposed, the polish rate is selectively reduced. At this point of time, the polishing is finished, thereby forming silicon substrate regions 121 to 124 provided with analysis surfaces, respectively.

Figure 12:
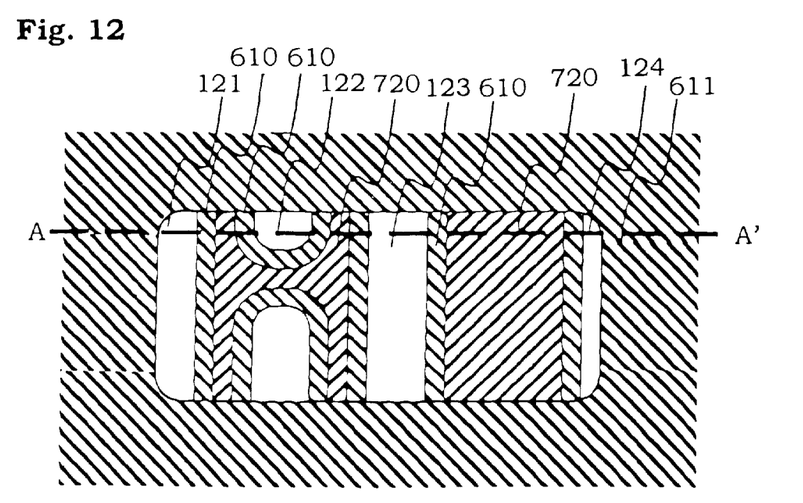
FIG. 12 is a schematic plan view of a major part of a sample manufactured by the process according to the present invention.

Thereafter, a plane configuration as shown in FIG. 12 is observed by using an observation apparatus such as a critical dimension measurement SEM.

Further, if the silicon substrate 100 has a repeated pattern of the predetermined region shown in FIG. 1, by optionally adjusting the height of the silicon substrate regions 116 and 117 at each predetermined region, plane configurations successive in a depth direction are obtained, and thus three-dimensional data is obtained.

Thus, the grooves are formed by a common process of manufacturing a semiconductor device, the periphery regions are reduced to a desired level by RIE while protecting the analysis region with the resist film, and then CMP is carried out to expose the analysis region surface accurately in the depth direction. Accordingly, the configuration of the device isolation regions formed in the semiconductor substrate is observed.

EXAMPLE 2

This example explains a process of manufacturing an electron microscopic sample for observing a configuration of electrodes formed on a semiconductor substrate.

First, on a p-type silicon substrate 100 provided as a semiconductor substrate, a silicon oxide film 800 of about 200 to 1000 nm thick is deposited as a first insulating film and a polysilicon film 900 of about 50 to 500 nm thick doped with phosphorus impurities is deposited as a first conductive film in this order. A resist is then applied thereon.

Figure 13:
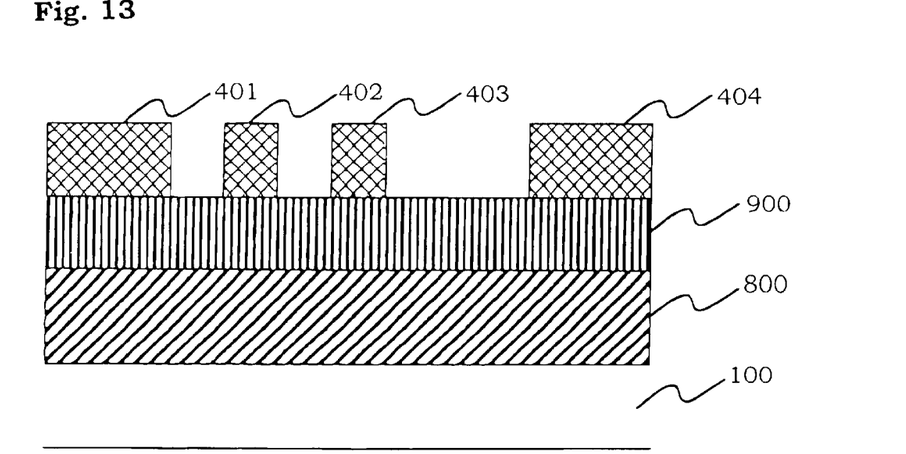
FIGS. 13 to 21 are other schematic sections of a major part for illustrating the process of manufacturing the electron microscopic sample of Example 2 according to the present invention.

Then, by using a light exposure mask pattern for defining electrodes each having a desired configuration (not shown), the resist is patterned by known photolithography and etching to leave resist films 401 to 404 as shown in FIG. 13.

Figure 14:
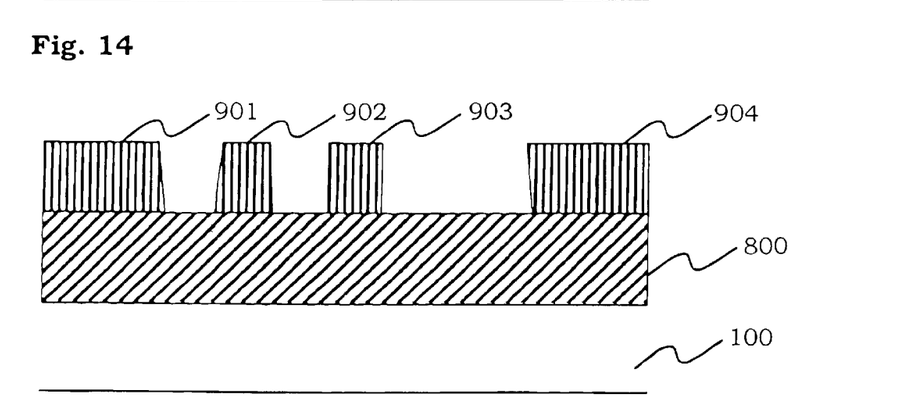

Using the obtained resist films 401 to 404 as a mask, the polysilicon film 900 is subjected to RIE to form polysilicon films 901 to 904 as shown in FIG. 14, which will serve as the electrodes. Thereafter, the resist films 401 to 404 are removed.

Figure 15:
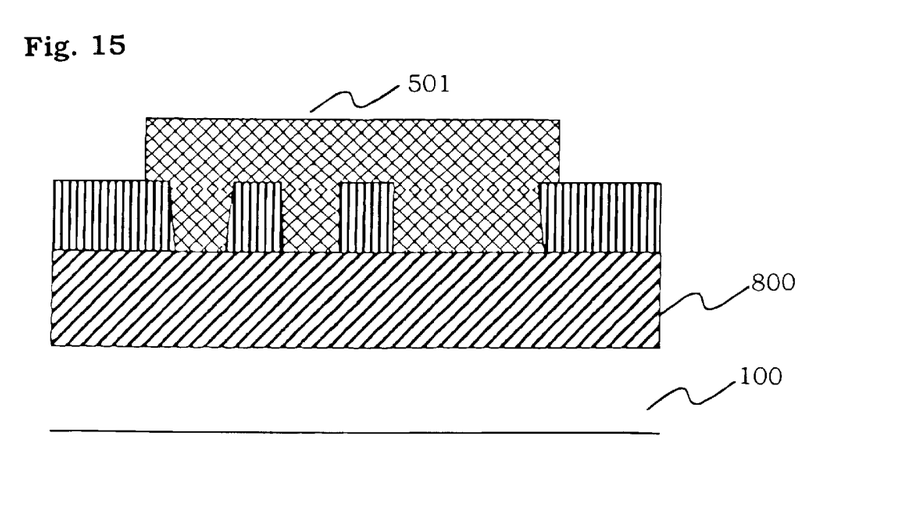

Then, a resist film 501 is formed to protect an analysis region as shown in FIG. 15.

Figure 16:
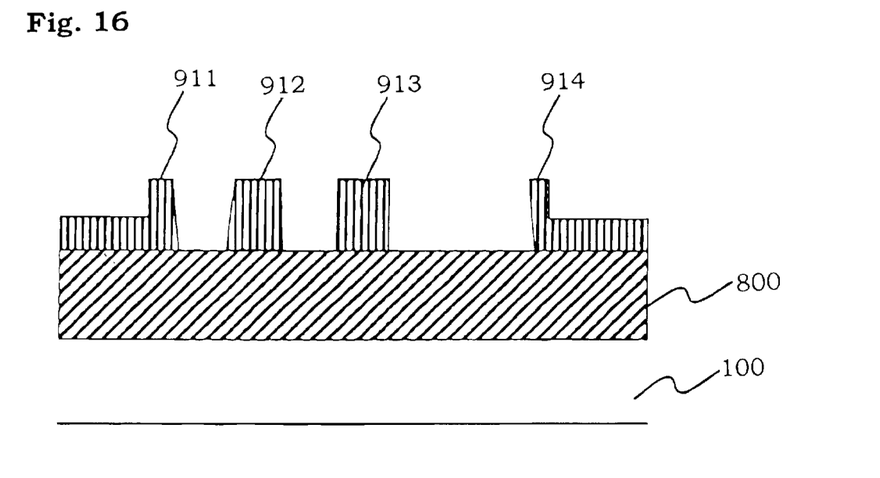

Using the resist film 501 as a mask, RIE is performed to reduce the electrodes in a region on the periphery of the analysis region by a thickness of about 100 nm while controlling the etching time, thereby forming polysilicon films 911 and 914 as shown in FIG. 16. In this step, the polysilicon films 911 and 914 are accurately provided while defining the etching depth with an alignment error of about 3 nm. Further, the polysilicon films 911 to 914 within the analysis region are protected by the resist film 501 against RIE.

Figure 17:
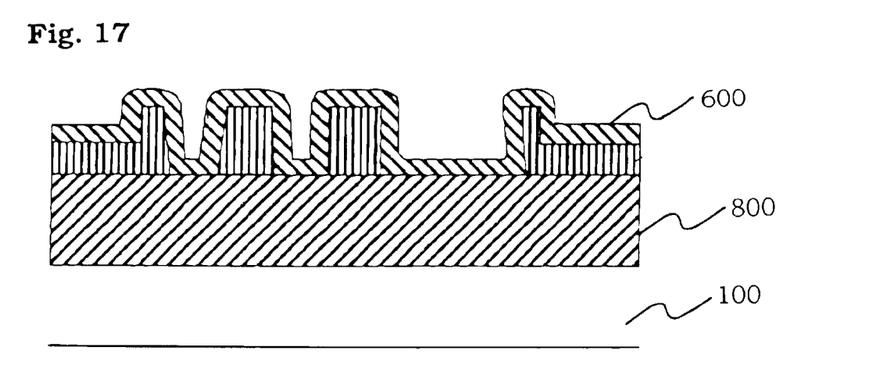
Figure 18:
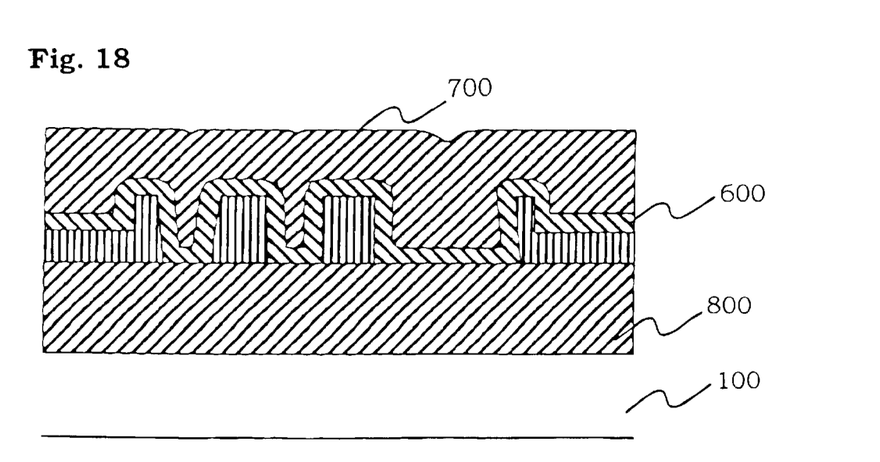

Then, as shown in FIG. 17, a silicon nitride film 600 of about 10 to 200 nm thick, which serves as a third mask layer and a polish stop layer, is deposited over the polysilicon films 911 to 914 and the silicon oxide film 800. Further, as shown in FIG. 18, a silicon oxide film 700 of about 100 to 1000 nm thick is deposited as a fourth mask layer on the third mask layer to fill concave portions between the electrodes.

Figure 19:
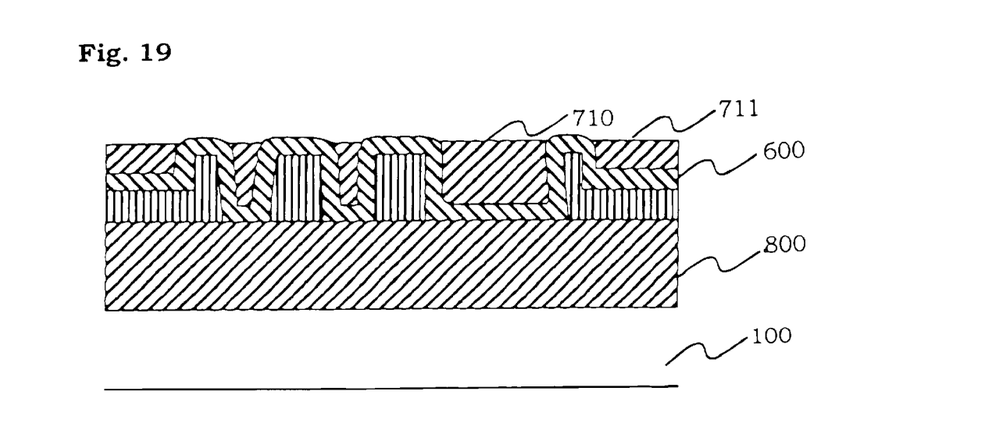

Then, the silicon oxide film 700 is etched back such that the silicon nitride film 600 is partially exposed, thereby silicon oxide films 710 are buried in the concave portions between the electrodes and silicon oxide films 711 are buried in the periphery regions around the analysis region as shown in FIG. 19.

Figure 20:
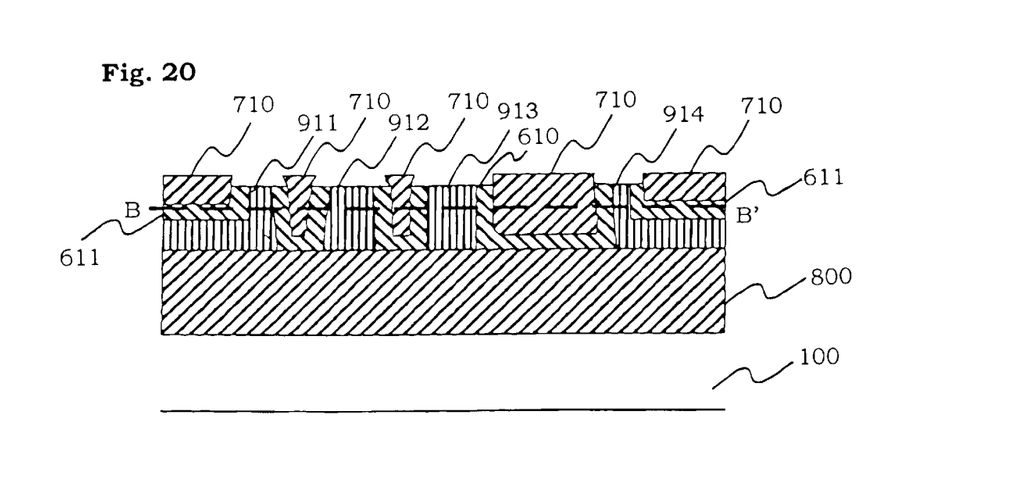

Then, using the silicon oxide films 710 and 711 as a mask, the exposed silicon nitride film 600 is selectively removed such that the surface of the polysilicon films 911 to 914 is exposed to form silicon nitride films 610 and 611 as shown in FIG. 20.

Figure 21:
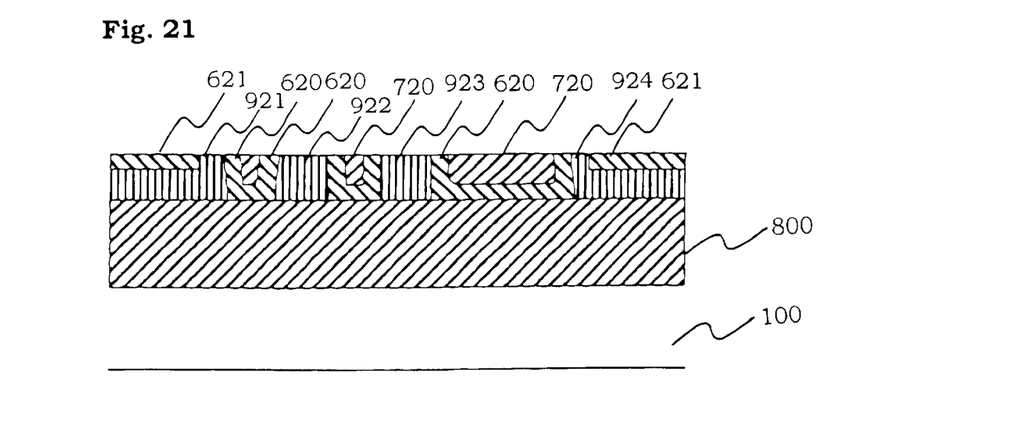

Then, as shown in FIG. 21, the polysilicon films 911 to 914 and the silicon oxide films 710 are subjected to CMP, for example, such that they are polished down to the level indicated by the broken line B–B' shown in FIG. 20, i.e., such that the surface of the silicon nitride film 611 is exposed. In this step, the silicon nitride films 610 and 611, which serve as the third mask layers and the polish stop layers and located on the sides of the electrodes in the analysis region, are polished by CMP at almost the same polish rate as the adjacent polysilicon films 911 to 914 and the silicon oxide films 710 and 711. When the silicon nitride films 611 which are formed on the polysilicon films 911 and 914 in the periphery region and laid in a horizontal direction with respect to the substrate surface are exposed, the polish rate is selectively reduced. At this point of time, the polishing is finished, thereby forming polysilicon films 921 to 924 provided with analysis surfaces, respectively.

Figure 22:
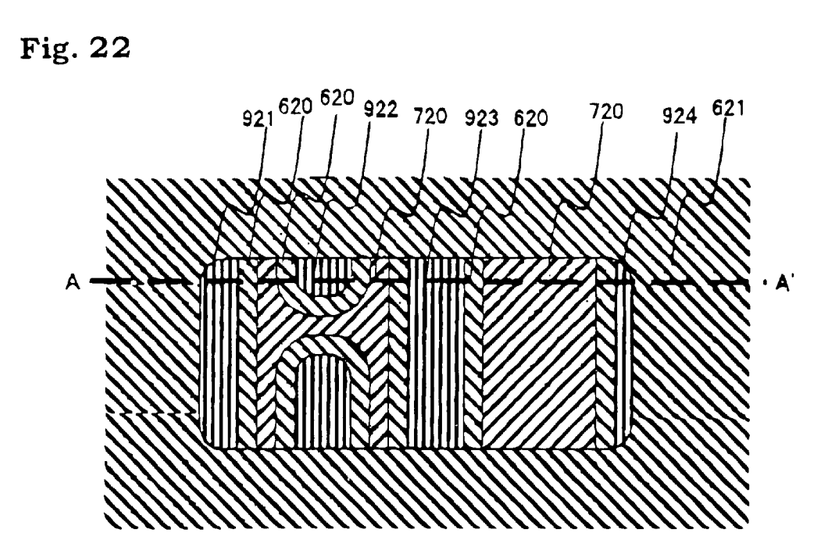
FIG. 22 is a schematic plan view of a major part of another sample manufactured by the process according to the present invention.

Thereafter, a plane configuration as shown in FIG. 22 is observed by using an observation apparatus such as a critical dimension measurement SEM.

By optionally adjusting the etching amount of the polysilicon films 911 and 914 in the same manner as in Example 1, a three-dimensional configuration is easily obtained and analyzed.

Thus, the electrodes are formed by a common process of manufacturing a semiconductor device, the electrodes in the periphery region are reduced by RIE to a desired level while protecting the analysis region with the resist, and then CMP is carried out to expose the analysis region surface accurately in the depth direction. Accordingly, the electrode configuration on the semiconductor substrate is observed.

According to the present invention, (a) forming a mask layer for covering an object region to be analyzed of a semiconductor layer or a conductive layer which has been patterned into a desired configuration; (b) reducing a periphery region around the object region to be analyzed in a depth direction by using the mask layer; (c) removing the mask layer and forming an etch stop layer over the object region to be analyzed and the periphery region; and (d) polishing the semiconductor layer or the conductive layer in the object region to be analyzed down to the level of the etch stop layer lying on the reduced periphery region. Therefore, can be provided a sample which allows highly accurate electron microscopic observation of a plane configuration of a region to which absolute alignment and etching have been performed. The sample eliminates the need of cleaving the wafer. Further, this sample facilitates the analysis of rounded edges of miniaturized patterns in a semiconductor device, as well as plane configurations of gate electrodes, active regions and device isolation regions.

In the case where a plurality of analysis regions are formed at plural regions, the analysis is carried out at the plural regions simultaneously, which reduces the analysis time.

Further, by varying the reduction amount of the analysis regions, the configurations are observed at optional depths. The obtained configuration data are combined to obtain a three-dimensional configuration easily with high accuracy.

Thus, according to the process of manufacturing the electron microscopic sample and the process of analyzing the semiconductor device, feedback to the manufacture of the semiconductor device is carried out in a short period with good accuracy, which allows improvement in device characteristics and reduction of manufacture costs.

What is claimed is:

1. A process of manufacturing an electron microscopic sample comprising:

(a) forming a mask layer for covering an object region to be analyzed of a semiconductor layer and/or a conductive layer which have/has been patterned into a desired configuration;

(b) reducing a periphery region surrounding the object region to be analyzed in a depth direction using the mask layer;

(c) removing the mask layer and forming an etch stop layer over the object region to be analyzed and the periphery region;

(d) polishing the semiconductor layer and/or the conductive layer in the object region to be analyzed down to the level of the surface of etch stop layer lying on the reduced periphery region; and (e) observing a plane configuration of a semiconductor device by using the electron microscopic sample obtained via at least steps (a) through (d).

2. A process according to claim 1, wherein, in the step (b), a reduction amount of the periphery region is smaller than a patterning depth of the semiconductor layer and/or the conductive layer.

3. A process according to claim 1, wherein, in the step (c), a film is formed on the etch stop layer and a surface thereof is flattened such that the film is buried between the semiconductor layers and/or the conductive layers that have/has been patterned.

4. A process according to claim 1, wherein a plurality of mask layers are formed on object regions to be analyzed of a semiconductor layer and/or a conductive layer which have/has been patterned into a desired configuration.

5. A process according to claim 4, wherein the plurality of object regions have a repeated pattern of the semiconductor layers and/or the conductive layers.

6. A process according to claim 4, wherein the periphery regions surrounded the object regions to be analyzed are reduced by a reduction amount varied among the plural regions and the semiconductor layer an/or the conductive layer lying on each of the object regions to be analyzed are/is polished in an amount corresponding to the varied reduction amount of the periphery region.

7. A process of analyzing a semiconductor device wherein a plurality of plane configurations of the semiconductor device are observed on an electron microscopic sample obtained by a process according to claim 1 and the obtained data is synthesized to analyze a three-dimensional configuration of the semiconductor device.

8. A process of manufacturing and analyzing an electron microscopic sample of a semiconductor device, the process comprising:

forming a mask layer for covering an object region of a semiconductor layer and/or a conductive layer which have/has been patterned into a desired configuration;

thinning a periphery region at least partially surrounding the object region to be analyzed in a depth direction using the mask layer, so as to form a reduced periphery region;

removing the mask layer and forming an etch stop layer over the object region and over at least part of the periphery region;

polishing the semiconductor layer and/or the conductive layer in the object region so as to expose at least part of the etch stop layer overlying the reduced periphery region; and observing the electron microscopic sample after said polishing via an electron microscope.

* * * * *